United States Patent [19]

Sugiyama et al.

[11] Patent Number: 4,597,943

[45] Date of Patent: Jul. 1, 1986

[54] APPARATUS FOR ANALYZING SOLID SAMPLE WITH SUPERCRITICAL FLUID

[75] Inventors: Kenkichi Sugiyama, Yokohama; Muneo Saito; Akio Wada, both of Hachioji, all of Japan

[73] Assignees: Morinaga & Co., Ltd., Tokyo; Japan Spectroscopic Co., Ltd., Hachioji, both of Japan

[21] Appl. No.: 676,200

[22] Filed: Nov. 29, 1984

[51] Int. Cl.[4] ............................................. G01N 1/22
[52] U.S. Cl. ...................................... 422/70; 73/23.1; 73/864.81; 73/864.83; 422/89
[58] Field of Search ................... 422/70, 89; 73/23.1, 73/864.81, 864.83

[56] References Cited

U.S. PATENT DOCUMENTS 4,155,683  5/1979  Mochizuki et al. ................. 417/269
4,300,393  11/1981 Stearns ............................ 73/864.81
4,351,802  9/1982  Baylis et al. ......................... 422/89

OTHER PUBLICATIONS

Ito et al., "Head Space Gas Chromatographic Method . . .", *Nippon Shokuhin Kogyo Gakkaishi*, vol. 30, No. 3, 1983, pp. 133–139.
Dennis R. Gere, "Supercritical Fluid Chromatography with Small Particle Diameter Packed Columns", *Anal. Chem.* 1982, 54, 736–740.
Rawdon et al., "Supercritical Fluid Chromatography as a Routine Analytical Technique", *International Laboratory* 1984, pp. 12–23.

*Primary Examiner*—Arthur Kellogg
*Attorney, Agent, or Firm*—Browdy and Neimark

[57]  ABSTRACT

An apparatus for analyzing a sample with a supercritical fluid includes a fluid container containing as an extraction solvent a fluid obtained by compressing and liquefying a substance which is a gas at ambient temperature and atmospheric pressure. A pump is provided for drawing the fluid from its container through a suction line and delivering it through a delivery line, while the heads of the pump are cooled by a cooling device. An extraction mechanism is provided for bringing the fluid in a supercritical state into contact with the sample to be analyzed and extracting a specific component or components from the sample. A trapping mechanism is provided downstream of the extraction mechanism for collecting the extracted component or components from the fluid. An analyzing mechanism can be connected to the trapping mechanism by changeover valves for analyzing the collected component or components.

8 Claims, 4 Drawing Figures

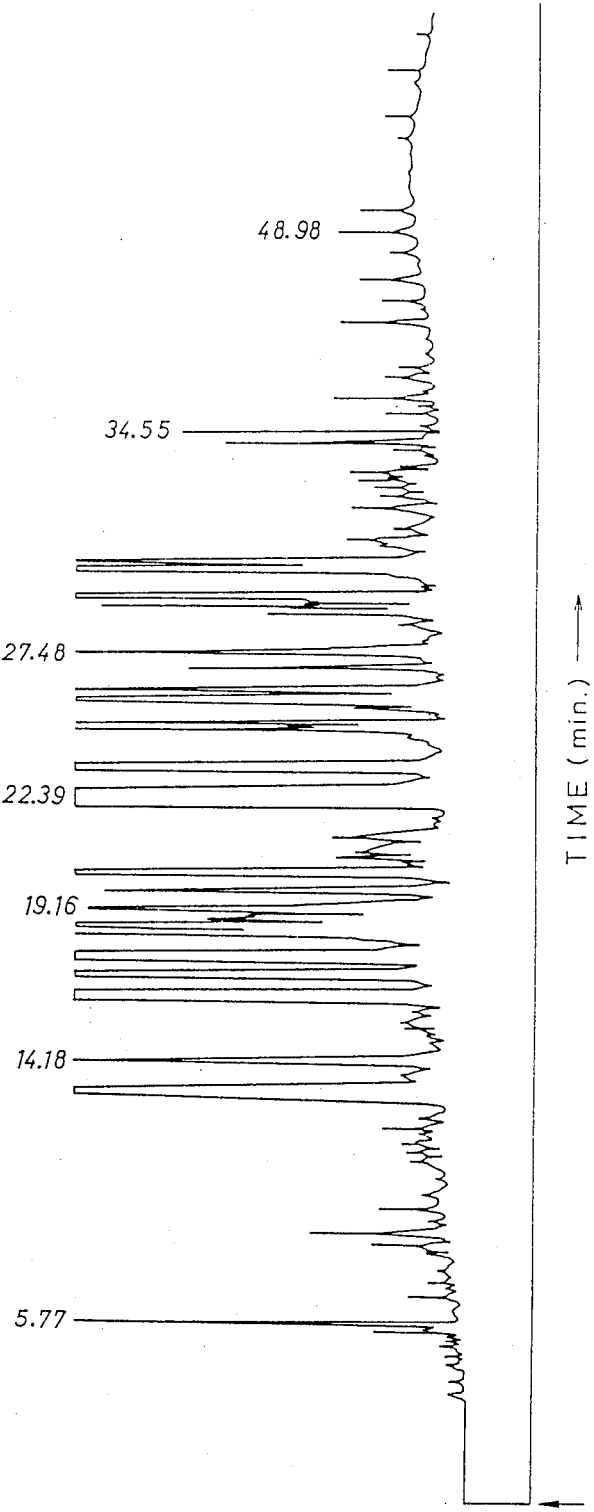

4,597,943

APPARATUS FOR ANALYZING SOLID SAMPLE WITH SUPERCRITICAL FLUID

BACKGROUND OF THE INVENTION

1. Field of the Invention

This invention relates to an apparatus for analyzing a sample with a supercritical fluid. More particularly, it relates to an apparatus of simple construction which employs a supercritical fluid for extracting certain components from a solid sample, and analyzing them.

2. Description of the Prior Art

While an organoleptic test by skilled persons has for a long time been relied upon for the identification and evaluation of the flavor (volatile components) of coffee bean powder, food, cosmetics, perfumes, etc., attention has recently come to be directed to the use of gas chromatography for the analysis and evaluation of those volatile components as described, for example, in "Nippon Shokuhin Kogyo Gakkaishi", vol. 30, No. 3, pages 133 to 139 (1983). According to this method, volatile components are collected from a sample by condensation or adsorption, and analyzed and evaluated by an ordinary gas chromatographic technique.

This gas chromatographic method, however, still has a lot of problems, since it employs a solid sample having a very low concentration of volatile components and has to wait for the volatilization of the volatile components for their collection. It requires a sample quantity which is as large as at least 10 g. It has a low degree of detection sensitivity. It requires a lot of time for collecting the volatile components. It involves a complicated procedure for the condensation or adsorption of the volatile components.

A supercritical fluid obtained by compressing and liquefying carbon dioxide or other substance which is a gas at ambient temperature and atmospheric pressure is characterized by its excellent ability to dissolve various kinds of substances. This characteristic is utilized in a known technique for extracting components from various substances as described, for example, in Anal. Chem., vol. 54, No. 4, pages 736 to 740, April 1982 and International Laboratory, pages 12 to 23, June 1984.

As a supercritical fluid is very liable to gasification, however, a lot of care is required for its transportation so that it may not gasify. For example, it is necessary to use a pump having a high compression ratio. An extremely large and complicated apparatus is, therefore, required for the analytical operation which employs a supercritical fluid, and is has hitherto been considered that a supercritical fluid is difficult to employ for analytical purpose.

SUMMARY OF THE INVENTION

Under these circumstances, it is an object of this invention to provide a practical, supercritical fluid analyzer, i.e., a practical apparatus for analyzing a sample with a supercritical fluid, and especially an apparatus which includes a very simple system for supplying a supercritical fluid to extract certain components from a sample and analyze them effectively.

This object is attained by an apparatus comprising (a) a fluid container containing as an extraction solvent a fluid obtained by compressing and liquefying a gaseous substance which is gaseous at ambient temperature and atmospheric pressure, (b) pressure pump means for drawing the fluid from the fluid container through a suction passage and delivering it through a delivery passage, preferably a pump of the reciprocating plunger type, (c) means for cooling the head of the pressure pump means, or preferably the pump of the reciprocating plunger type, (d) an extraction mechanism by which the fluid supplied through the delivery passage is brought into contact with a solid sample in a supercritical state to extract specific components from the sample, (e) a trapping mechanism provided downstream of the extraction mechanism for separating and collecting from the fluid the components extracted by the extraction mechanism, and (f) a mechanism adapted for connection to the trapping mechanism by changeover valve means for analyzing the components leaving the trapping mechanism.

In accordance with one advantageous embodiment of the invention, the suction line has a passage portion consisting of at least two branch lines, one of the branch lines defining a passageway for the fluid, while the other branch line having a solvent tank containing an entrainer assisting the extraction, the solvent tank being divided into two chambers by a movable or deformable partition, one of the chambers containing the entrainer, while the fluid flows into the other chamber to exert pressure on the partition to force the entrainer out of the one chamber, the one branch line having a valve, while another valve is provided on the other branch line downstream of the solvent tank, the valves being operable to supply the fluid and the entrainer in a predetermined proportions so that a mixture of the fluid and the entrainer may be supplied to the pump means.

According to a preferred form of the invention, the analyzing mechanism has a discharge line connected to the suction line between the pump means and a point at which the branch lines join each other to form the mixture, the discharge line having a drain valve which can be switched over to effect alternatively the discharge of the fluid from the analyzing apparatus through the discharge line and the recirculation of the fluid to the suction line.

In the analyzing apparatus constructed as described above, the analyzing mechanism comprises a liquid or gas chromatograph including a separating column and a detector.

According to another advantageous embodiment of the invention, the changeover valve means or selector valve means comprises a first changeover valve (selector valve) and a second changeover valve (selector valve), the delivery line and the analyzing mechanism being connected to the first changeover valve, the first and second changeover valves being connected to each other by two connecting lines, the trapping mechanism being located on one of the connecting lines, the second changeover valve forming a closed circuit in which the extraction mechanism is provided, the first and second changeover valves being operable to effect alternatively the connection of the delivery line, the extraction mechanism and the trapping mechanism and the connection of the trapping mechanism to the analyzing mechanism.

BRIEF DESCRIPTION OF THE DRAWINGS

FIG. 4 is a gas chromatogram obtained by employing the apparatus of this invention.

DETAILED DESCRITPTION OF THE PREFERRED EMBODIMENTS

The invention will now be described more specifically by way of example with reference to the drawings.

Figure 1:
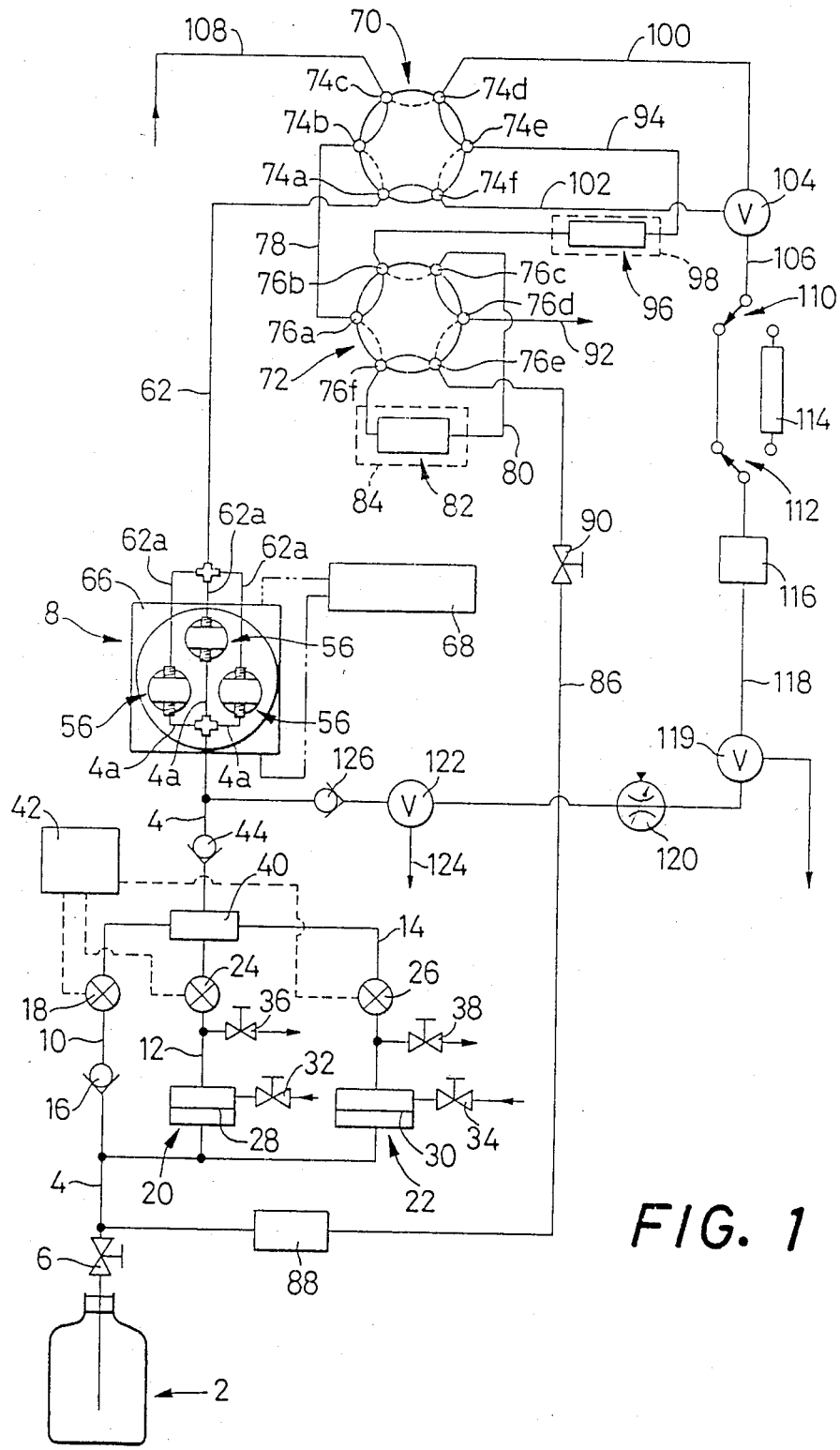
FIG. 1 is a schematic diagram of an apparatus embodying this invention.

Referring first to FIG. 1, there is diagrammatically shown an analyzer embodying this invention. It includes a $CO_2$ cylinder or bottle 2 containing liquefied carbon dioxide (fluid) obtained by compressing and liquefying carbon dioxide which is a gas at ambient temperature and atmospheric pressure. A suction pipe 4 extends into the $CO_2$ bottle 2 and has an end located in the vicinity of its bottom. The suction pipe 4 is provided with a valve 6 which is operable to draw liquefied carbon dioxide from the bottle 2 and supply it to a pump 8 through the suction pipe 4.

The suction pipe 4 has three branch lines 10, 12 and 14. The branch line 10 has a check valve 16 and a solenoid valve 18. The branch line 12 has a solvent tank 20 and a solenoid valve 24 downstream of the solvent tank 20. The branch line 14 likewise has a solvent tank 22 and a solenoid valve 26 downstream of the solvent tank 22. The solvet tank 20 has a movable or deformable partition 28 which divides the tank into two chambers in a gastight and liquidtight fashion. The solvent tank 22 likewise has a movable or deformable partition 30 which divides the tank into two chambers in a gastight and liquidtight fashion. A solvent assisting extraction is supplied into one of the chambers of the solvent tank 20 through a valve 32, while a different solvent assisting extraction is supplied into one of the chambers of the solvent tank 22 through a valve 34. A drain valve 36 is provided for draining purposes when the solvent is supplied into the solvent tank 20, and a drain valve 38 when the solvent is supplied into the solvent tank 22.

The solvents are forced out of the solvent tanks 20 and 22 as the liquefied carbon dioxides flows into the other chambers of the tanks through the suction pipe 4, and supplied into a mixing tank 40 by means of the suction force of the pump 8 in quantities controlled by the solenoid valves 24 and 26. The mixing tank 40 is also supplied through the branch line 10 with the liquefied carbon dioxide in a quantity controlled by the solenoid valve 18. The solenoid valves 18, 24 and 26 are controlled by a control device 42 so that the quantities of liquefied carbon dioxide and one or two extraction-assisting solvents flowing into the mixing tank 40 per unit time may have an appropriate ratio to form a fluid mixture having an appropriate concentration. The fluid mixture is supplied to the pump 8 through a check valve 44. The mixing ratio of the liquefied carbon dioxide and solvents can be varied as desired if the durations of opening of the solenoid valves 18, 24 and 26 are appropriately changed by the control device 42. This ratio can also be varied with the lapse of time. The control of the valves by the control device 42 is usually effected at a cycle of at least 0.1 second.

Figure 2:
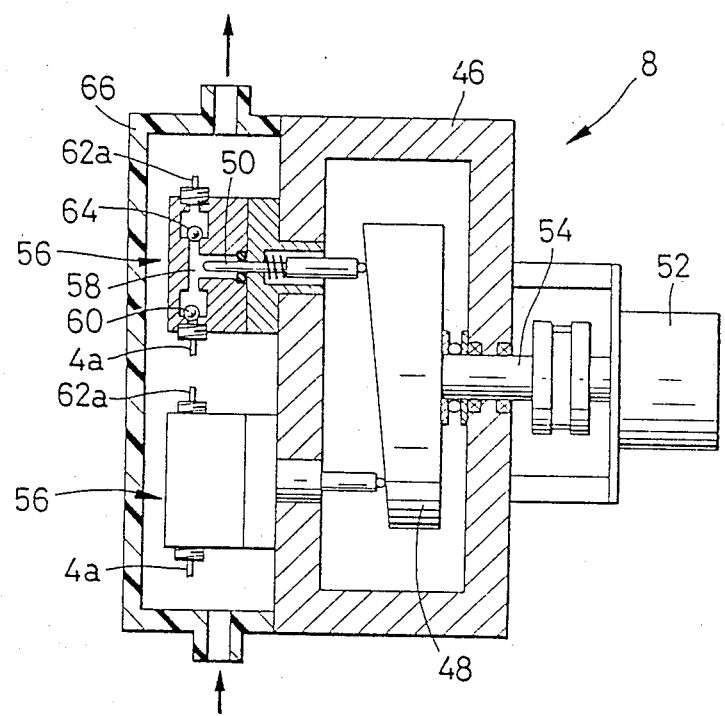
FIG. 2 is an enlarged cross sectional view of a pump employed in the apparatus of FIG. 1.

Referring to FIG. 2, the pressure pump means or pump 8 has three axially reciprocable plungers 50 provided in a housing 46 and maintaining a pin-point contact with a rotatable slanting plate 48. The plungers 50 are located on a circle and have an angular distance of 120° from one another. The slanting plate 48 comprises a cut portion of a column having a cut surface lying at an angle to the longitudinal axis of the column so that its rotation may give axial movement to the plungers 50 contacting the cut surface. The slanting plate 48 is rotated with a rotary shaft 54 supported by bearings and driven by a variable speed motor 52 supported on the housing 46 and connected to a speed reducing mechanism. Three pump units 56 are supported on the housing 46. Each plunger 50 is reciprocally movable into a solution chamber (pumping chamber) 58 in one of the pump units 56. Each pump unit 56 has a suction valve 60 in a port to which a suction pipe 4a is connected, and a delivery valve 64 in a port to which a delivery pipe 62a is connected. The suction pipes 4a of the three pump units 56 are connected to the suction pipe 4 and the delivery pipes 62a thereof to a main delivery pipe 62, as shown in FIG. 1.

The construction and operation of the pump 8 of the reciprocating plunger type are detailed in U.S. Pat. No. 4,155,683 issued to one of the inventors of this invention et al. The rotation of the slanting plate 48 by the motor 52 causes the axial reciprocation of the plungers 50 in the pump units 56 one after another (in a clockwise or counterclockwise order in FIG. 1), whereby the pump 8 continuously draws the fluid through the suction pipe 4 and delivers it through the delivery pipe 62.

The pump 8 has a cooling jacket 66 attached to the front side of the housing 46 and covering the pump units 56. A cooling fluid, which may be a gas or liquid, is supplied from a cooler 68 to the cooling jacket 66, as shown in FIG. 1, to cool the pump heads of the pump 8, i.e., the pump portions in which the fluid is compressed (i.e., the solution chambers 58 of the pump units 56 into which the plungers 50 are movable). This cooling effectively prevents the gasification of the fluid, which consists mainly of liquefied carbon dioxide, when it is compressed in the chambers 58, and thereby ensures normal operation of the pump. Moreover, additional cooling of connection tubing, which is connected to the pump heads of the pump 8, located in the vicinity of the pump heads, for example suction pipes 4a, delivery pipes 62a, etc., is more effective for preventing the gasification of the fluid.

A first six-way valve (i.e. six-port valve) 70 and a second six-way valve (i.e. six-port valve) 72, which define a changeover valve means, are provided downstream of the delivery pipe 62 and connected in series to each other. As is well known, each of the six-way valves 70 and 72 has six ports 74a to 74f or 76a to 76f and each port can be connected to one of the two adjoining ports. In other words, each valve enables changeover between the port connection shown by solid lines in FIG. 1 and the port connection shown by broken lines. The delivery pipe 62 is connected to the port 74a of the first six-way valve 70 and the first six-way valve 70 is connected to the second six-way valve 72 by a connecting line 78 extending from the port 74b of the former to the port 76a of the latter.

A closed circuit 80 is formed between the port 76c of the second six-way valve 72 and the port 76f which can be connected to the port 76a. The closed circuit 80 has a sample cartridge 82 in which the sample to be analyzed can be placed. The sample cartridge 82 has a constant temperature maintained by a constant temperature tank 84. The fluid is supplied into the sample cartridge 82 through the delivery pipe 62, the first six-way valve 70, the connecting line 78 and the closed circuit 80 and brought into contact with the sample, in a supercritical state, i.e., at temperature and pressure above its critical point to extract specific components from the sample.

A purging gas line 86 is connected to the port 76e of the second six-way valve 72 which can be connected to the port 76f. Liquefied carbon dioxide can be supplied from the bottle 2 to the purging gas line 86 through the valve 6 and the suction pipe 4 and into the sample cartridge 82 through a pressure reducing valve 88, a valve 90 and the ports 76e and 76f to purge the sample cartridge 82 and the closed circuit 80. The carbon dioxide which has purged the sample cartridge 82 and the closed circuit 80 is discharged through a drain line 92 connected to the port 76d which can be connected to the port 76c to which the closed circuit 80 is connected.

A trap line 94 is provided between the port 76b adjoining the port 76c to which the closed circuit 80 is connected and the port 74e of the first six-way valve 70. The trap line 94 has a trap column 96 filled with an appropriate material, such as an adsorbent. The components extracted by the supercritical fluid in the sample cartridge 82 are separated from the fluid while the fluid introduced through the closed circuit 80, the ports 76c and 76b and the trap line 94 is caused to pass through the trap column 96. A constant temperature tank 98 is provided for maintaining the trap column 96 at a constant temperature so that the components collected by the material filling the trap column 96 may be released therefrom when required.

Feed lines 100 and 102 are connected to the ports 74d and 74f, respectively, which can be connected to the port 74e to which the trap line 94 is connected. The feed lines 100 and 102 can be selectively connected to an analyzing line 106 by a three-way valve 104. A mobile phase supply line 108 is connected to the port 74c between the ports 74b and 74d to supply a liquid or gaseous mobile phase from a pump for liquid chromatography or a source of gas for gas chromatography.

The analyzing line 106 can be connected to a separating column 114 by valves 110 and 112 so that the mobile phase containing the specific components and introduced through the analyzing line 106 may be developed in the separating column 114 by a liquid or gas chromatographic technique and separated into the individual components which are detected by a detector 116 located downstream of the column 114. In the event the mobile phase introduced into the analyzing line 106 contains only one component to be analyzed, the valves 110 and 112 are positioned as shown in FIG. 1 to supply the mobile phase directly to the detector 116, e.g. an UV detector.

A discharge line 118 extends from the detector 116 and has a discharge valve 119 which is used to discharge the fluid when it is not necessary to apply pressure thereto. In the event it is necessary to apply pressure to the fluid, a servo pressure controller 120 is provided for controlling the pressure of the fluid upstream thereof and a three-way valve 122 is provided for discharging the fluid through a drain line 124, or for connecting the discharge line 118 to the suction pipe 4 between the mixing tank 40 and the pump 8 through a check valve 126 so that the fluid in the discharge line 118 may be drawn by the pump 8 through the suction pipe 4 and delivered into the delivery line 62 to repeat a cycle of extraction and trapping.

While in the apparatus as hereinabove described, the fluid or liquefied carbon dioxide used as an extraction solvent is continuously drawn from the $CO_2$ bottle 2 by the pump 8 through the suction pipe 4 and delivered into the delivery pipe 62, its gasification can be effectively prevented by the use of the pump 8 of the reciprocating plunger type and the cooling of its pump heads. The pump 8 of the reciprocating plunger type has a compression ratio of, say, two or three times and never exceeding several times. According to a salient feature of this invention, a pump having such a low compression ratio can be effectively used to deliver a liquefied fluid having a high pressure (about 70 atm. in the case of liquefied carbon dioxide), only if the pump heads are cooled. If the pump heads are not cooled, liquefied carbon dioxide is difficult to feed through the pump 8. Although the foregoing description has been based on the use of liquefied carbon dioxide as an extraction solvent, it is also possible to use another fluid obtained by compressing and liquefying another substance that is a gas at ambient temperature and atmospheric pressure, e.g. propane or ethylene.

The solvent tanks 20 and 22 are provided on the branch lines 12 and 14, respectively, and each tank contains a solvent assisting extraction, i.e., an entrainer improving the efficiency of extraction by liquefied carbon dioxide, such as ethanol, hexane or water. The solenoid valves 18, 24 and 26 are controlled to provide a fluid mixture having an appropriate mixing ratio, and the fluid mixture is supplied through the pump 8 to perform an effective extraction of the specific components from the sample in the sample cartridge 82. No booster pump or the like is employed to supply the entrainers into the high pressure suction pipe 4, but the pressure of the liquefied carbon dioxide acting on the entrainers in the solvent tanks 20 and 22 via the partitions 28 and 30 is effectively utilized to supply the entrainers to the mixing tank 40 through the solenoid valves 24 and 26. This arrangement drastically simplifies the equipment for introducing the entrainers into the high pressure line.

In the event the specific components are extracted from the sample in the sample cartridge 82 by a supercritical fluid comprising liquefied carbon dioxide, the ports of the first and second six-way valves 70 and 72 are connected as shown by the broken lines in FIG. 1 and the fluid is supplied from the delivery pipe 62 to the sample cartridge 82 in the closed circuit 80 through the ports 74a and 74b, the connecting line 78 and the ports 76a and 76f. The fluid which has extracted the specific components from the sample in the sample cartridge 82 is introduced into the trap line 94 through the ports 76c and 76b and the components are separated from the fluid in the trap column 96. The fluid, from which the components have been separated, is caused to flow into the discharge line 118 through the ports 74e and 74f, the feed line 102, the three-way valve 104 and the analyzing line 106, and discharged through the three-way valve 122 or recycled therethrough into the suction pipe 4.

The components collected from the fluid are released from the trap column 96 and separated into the individual components in the separating column 114, and the individual components are detected by the detector 116. Alternatively, if only one component is involved for analysis, it is passed directly to the detector 116. The release of the components from the trap column 96 is effected by the control of its temperature by the constant temperature tank 98. Alternatively, it can be effected by connecting the ports of the first and second six-way valves 70 and 72 as shown by the solid lines in FIG. 1 and introducing a liquid or gas chromatographic mobile phase into the trap column 96 through the mobile phase supply line 108. The components released from the trap column 96 are caused to flow with the mobile phase through the ports 74e and 74d, the feed line 100, the three-way valve 104, the analyzing line 106, the valve 110, the separating column 114, the valve 112 and the detector 116.

According to the apparatus of this invention as hereinabove described, a fluid capable of forming a supercritical fluid is effectively supplied by the pump 8 into the sample cartridge 82 defining an extraction mechanism in which the fluid forms a supercritical fluid and effectively extracts the specific components from the sample to be analyzed, and the components are separated from the fluid in the trap column 96 on the trap line 94 and conveyed by a separately introduced mobile phase to an analyzing mechanism defined by the separating column 114 and the detector 116. The apparatus, therefore, enables the analysis of a solid sample which has hitherto been considered difficult, and the analysis and evaluation of the volatile components of foods, chemicals, perfumes, fats, etc., while employing the sample in a very small quantity.

Figure 3:
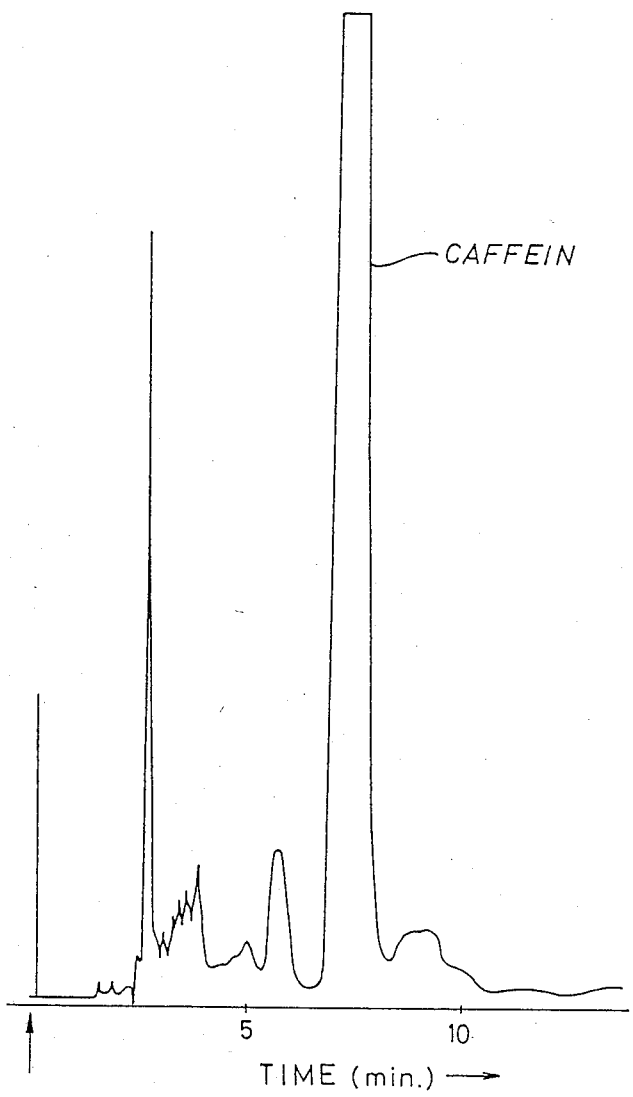
FIG. 3 is a liquid chromatogram obtained by employing the apparatus of this invention.

FIGS. 3 and 4 show by way of example the chromatograms obtained by employing the apparatus of this invention for analyzing the flavor of coffee bean powder. FIG. 3 shows the results of liquid chromatography, and FIG. 4 the results of gas chromatography. The conditions of the analyses were as follows:

| (1) Conditions of Extraction | |
|---|---|
| Sample cartridge (82) | |
| Sample weight: | 0.4 g. |
| Cartridge scale: | 4.6 mm dia. by 5 cm long. |
| Temperature: | 48° C. |
| $CO_2$: | Supplied at a pressure of 120 $kg/cm^2$ and a flow rate of 5 ml/min. |
| Trap column (96) | |
| Packing agent: | Micro-beads of silica (200 mesh). |
| Column scale: | 4.6 mm dia. by 50 cm long. |
| Temperature: | 10° C. |
| (2) Conditions of High-Performance Liquid Chromatography | |
| Separating column: | Packed with Fine-pak-silica ® (JAPAN SPECTROSCOPIC CO., LTD.) |
| Column scale: | 4.6 mm dia. by 25 cm long. |
| Mobile phase solvent: | Methanol/water = 45/55. |
| Detector: | UV detector (UVIDEC-II ®; JAPAN SPECTROSCOPIC CO., LTD.), 280 nm, 0.64 AUFS. |
| (3) Conditions of Gas Chromatography | |
| Separating column: | Thermon 600T (Shimazu Seisakusho LTD. Japan) |
| Column scale: | 0.5 mm dia. by 50 m. |
| Carrier: | 1 kg, split 1:30. |
| Temperature: | 70° C. to 210° C. at 4° C. /min. |
| Absorbing column: | 3 mm dia. by 20 cm long [tenax GC (AKZO Research Laboratories) 15 cm], 200° C., 1 min., inlet. |

As is obvious from FIGS. 3 and 4, the apparatus of this invention enables the effective extraction and analysis of the specific components by a supercritical fluid, while employing the sample in a quantity which is as small as 0.4 g.

While the invention has been described with reference to a preferred embodiment thereof, it is to be understood that it is not intended for limiting the scope of this invention, but that modifications or variations may be easily made by anybody of ordinary skill in the art without departing from the spirit and scope of this invention which are defined by the appended claims.

For example, while the pump 8 of the reciprocating plunger type can advantageously be used, it is equally possible to employ other pump means. Although the pump 8 has been described as comprising three pump units 56, it is possible to use a pump of the reciprocating plunger type havng one or two pump units or four or more pump units. Although the suction pipe 4 has been described as having three branch lines 10, 12 and 14, it is sufficient to provide two branch lines if only one kind of entrainer is employed. It is, of course, appropriate to provide four or more branch lines if required. Moreover, a wide variety of modifications may be possible for the cooler which supplies the cooling fluid to the cooling jacket 66 on the pump housing 46, or for the first and second six-way valves.

While the constant temperature tanks 84 and 98 have been shown only for the sample cartridge 82 and the trap column 96, respectively, it is desirable to control the temperature of the closed circuit 80 and the trap line 94 too, in order to maintain the supercritical state effectively. It would, moreover, be advisable to control the temperature of the six-way valves 70 and 72 and the associated lines if required.

What is claimed is:

1. An apparatus for analyzing a solid sample with a supercritical fluid comprising:
   a fluid container containing as an extraction solvent a fluid obtained by compressing and liquefying a substance which is a gas at ambient temperature and atmospheric pressure;
   a pump of a reciprocating plunger type for drawing said fluid from said fluid container through a suction line and delivering it through a delivery line;
   means for cooling a pump head portion of said pump to prevent gasification of said fluid;
   extraction means for bringing said fluid supplied through said delivery line into contact with the sample, in a supercritical state, to extract at least one component from said sample;
   trapping means provided downstream of said extraction means for collecting said at least one component from said fluid; and
   a chromatograph which can be connected to said trapping means by changeover valve means and which comprises a separating column, distinct from said trapping means for separating said at least one collected component from each other if said at least one component is at least two components, and comprises a detector for detecting said at least one component, said chromatograph further comprising means for passing said at least one component from said trapping means directly to said detector if said at least one component is only one component.

2. The apparatus as set forth in claim 1, wherein said pump means comprises a pump of the reciprocating plunger type.

3. The apparatus as set forth in claim 1, wherein said suction line has a passage portion consisting of at least two branch lines, one of said branch lines defining a passageway for said fluid, while the other branch line having a solvent tank containing an entrainer assisting said extraction, said solvent tank being divided into two chambers by a movable or deformable partition, one of said chambers containing said entrainer, while said fluid flowing into the other chamber to exert pressure on said partition to force said entrainer out of said one chamber, said one branch line having a valve, while another valve being provided on said other branch line downstream of said solvent tank, said valves being operable to supply said fluid and said entrainer in a predetermined proportion so that a mixture of said fluid and said entrainer may be supplied to said pump.

4. The apparatus as set forth in claim 3, wherein said analyzing means has a discharge line connected to said suction line between said pump and a point at which said branch lines join each other to form said mixture, said discharge line having a drain valve which can be switched over to effect alternatively the discharge of said fluid from said detector through said discharge line and the recirculation of said fluid into said suction line.

5. The apparatus as set forth in claim 1, wherein said analyzing mechanism comprises a liquid or gas chromatograph including a separating column and a detector.

6. The apparatus as set forth in claim 1, wherein said changeover valve means comprises a first changeover valve and a second changeover valve, said delivery line and said chromatograph being connected to said first changeover valve, said first and second changeover valves being connected to each other by two connecting lines, said trapping means being located on one of said connecting lines, said second changeover valve forming a closed circuit in which said extraction means is provided, said first and second changeover valves being operable to effect alternatively the connection of said delivery line, said extraction means and said trapping means and the connection of said trapping mechanism to said chromatograph.

7. The apparatus as set forth in claim 1, wherein said extraction and trapping means and the lines associated therewith are all provided with a temperature control device.

8. An apparatus for analyzing a sample with a supercritical fluid, comprising:

a fluid container containing as an extraction solvent a fluid obtained by compressing and liquefying a substance which is a gas at ambient temperature and atmospheric pressure;

pump means for drawing said fluid from said fluid container through a suction line and delivering it through a delivery line, said suction line having a passage portion consisting of at least two branch lines, one of said branch lines defining a passageway for said fluid while the other branch line has a solvent tank containing an entrainer assisting said extraction, said solvent tank being divided into two chambers by a movable or deformable partition, one of said two chambers containing said entrainer, while said fluid flows into the other chamber to exert pressure on said partition to force said entrainer out of said one chamber, said one branch line having a valve, while another valve is provided on said other branch line downstream of said solvent tank, said valves being operable to supply said fluid and said entrainer in a predetermined proportion so that a mixture of said fluid and said entrainer may be supplied to said pump means;

means for cooling pump heads of said pump means;

extraction means for bringing the fluid supplied through said delivery line into contact with the sample, in a supercritical state, to extract at least one component from said sample;

trapping means provided downstream of said extraction means for collecting said at least one component from said fluid; and analyzing means which can be connected to said trapping means by changeover valve means for analyzing said collected component from said trapping means.

* * * * *